US011017884B2

(12) United States Patent
Soon-Shiong

(10) Patent No.: US 11,017,884 B2
(45) Date of Patent: May 25, 2021

(54) DISCOVERY ROUTING SYSTEMS AND ENGINES

(71) Applicant: Nant Holdings IP, LLC, Culver City, CA (US)

(72) Inventor: Patrick Soon-Shiong, Los Angeles, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 0 days.

(21) Appl. No.: 16/450,450

(22) Filed: Jun. 24, 2019

(65) Prior Publication Data

US 2019/0325994 A1 Oct. 24, 2019

Related U.S. Application Data

(60) Division of application No. 16/153,563, filed on Oct. 5, 2018, now Pat. No. 10,332,618, which is a
(Continued)

(51) Int. Cl.
*G16B 50/00* (2019.01)
*G16H 80/00* (2018.01)
(Continued)

(52) U.S. Cl.
CPC ............ *G16B 50/00* (2019.02); *G06F 19/00* (2013.01); *G16H 50/20* (2018.01); *G16H 80/00* (2018.01); *G16Z 99/00* (2019.02)

(58) Field of Classification Search
CPC ......... G06N 19/28; G16H 50/20; G16H 80/00
(Continued)

(56) References Cited

U.S. PATENT DOCUMENTS 7,424,619 B1 * 9/2008 Fan ...................... G06F 21/552
 713/188
7,499,903 B2 3/2009 Nevin et al.
(Continued)

FOREIGN PATENT DOCUMENTS

CN 1398376 A 2/2003
CN 101517581 A 8/2009
(Continued)

OTHER PUBLICATIONS

Huang, Zhengxing, Xudong Lu, and Huilong Duan. "Anomaly detection in clinical processes." AMIA Annual Symposium Proceedings. vol. 2012. American Medical Informatics Association, 2012.*
(Continued)

*Primary Examiner* — Mark Holcomb
(74) *Attorney, Agent, or Firm* — Mauriel Kapouytian Woods LLP; Elaine K. Lee; Andrew A. Noble

(57) ABSTRACT

The inventive subject matter provides apparatus, systems, and methods that improve on the pace of discovering new practical information based on large amounts of datasets collected. In most cases, anomalies from the datasets are automatically identified, flagged, and validated by a cross-validation engine. Only validated anomalies are then associated with a subject matter expert who is qualified to take action on the anomaly. In other words, the inventive subject matter bridges the gap between the overwhelming amount of scientific data which can now be harvested and the comparatively limited amount analytical resources available to extract practical information from the data. Practical information can be in the form of trends, patterns, maps, hypotheses, or predictions, for example, and such practical information has implications in medicine, in environmental
(Continued)

sciences, entertainment, travel, shopping, social interactions, or other areas.

20 Claims, 5 Drawing Sheets

Related U.S. Application Data continuation of application No. 14/445,025, filed on Jul. 28, 2014, now Pat. No. 10,114,925.

(60) Provisional application No. 61/859,137, filed on Jul. 26, 2013.

(51) Int. Cl.
  *G16H 50/20* (2018.01)
  *G16Z 99/00* (2019.01)
  *G06F 19/00* (2018.01)

(58) Field of Classification Search
  USPC .......................................................... 705/2–4
  See application file for complete search history.

(56) References Cited

U.S. PATENT DOCUMENTS

| | | | |
|---|---|---|---|
| 8,090,592 B1* | 1/2012 | Goodall | G06Q 10/063 |
| | | | 705/2 |
| 10,114,925 B2 | 10/2018 | Soon-Shiong | |
| 10,332,618 B2 | 6/2019 | Soon-Shiong | |
| 2004/0122790 A1 | 6/2004 | Walker et al. | |
| 2006/0073496 A1* | 4/2006 | O'Toole | G01N 33/6896 |
| | | | 435/6.15 |
| 2006/0242035 A1 | 10/2006 | Corbett et al. | |
| 2008/0091471 A1 | 4/2008 | Michon et al. | |
| 2009/0034810 A1 | 2/2009 | Oakley | |
| 2010/0280847 A1* | 11/2010 | Schaffer | G16H 50/20 |
| | | | 705/3 |
| 2010/0293130 A1 | 11/2010 | Stephan et al. | |
| 2010/0324938 A1* | 12/2010 | Ennett | G16H 10/60 |
| | | | 705/3 |
| 2011/0049374 A1 | 3/2011 | Omi | |
| 2011/0077965 A1* | 3/2011 | Nolte | G06Q 10/10 |
| | | | 705/3 |
| 2011/0188743 A1 | 8/2011 | Urushiya | |
| 2012/0008838 A1 | 1/2012 | Guyon et al. | |
| 2012/0041575 A1 | 2/2012 | Maeda et al. | |
| 2012/0084092 A1* | 4/2012 | Kozuch | G06Q 50/22 |
| | | | 705/2 |
| 2012/0136676 A1 | 5/2012 | Goodall et al. | |
| 2012/0137367 A1 | 5/2012 | Dupont et al. | |
| 2012/0185275 A1* | 7/2012 | Loghmani | G06F 19/328 |
| | | | 705/3 |
| 2012/0231959 A1 | 9/2012 | Elton et al. | |
| 2013/0091545 A1 | 4/2013 | Macdonald et al. | |
| 2014/0316220 A1* | 10/2014 | Sheldon | A61B 5/0205 |
| | | | 600/301 |
| 2014/0359363 A1* | 12/2014 | Biem | G06F 11/3024 |
| | | | 714/37 |

FOREIGN PATENT DOCUMENTS

| | | |
|---|---|---|
| JP | 2009034517 A | 2/2009 |
| JP | 2011048759 A | 3/2011 |
| JP | 2011156272 A | 8/2011 |
| WO | 2011/139345 A2 | 11/2011 |
| WO | 2013/062505 A1 | 5/2013 |
| WO | 2013/090910 A2 | 6/2013 |
| WO | 2014/008434 A2 | 1/2014 |

OTHER PUBLICATIONS

International Search Report and Written Opinion issued in International Application No. PCT/US2014/057885 dated Apr. 21, 2015, 9 pages.
Schrimpe-Rutledge et al., "Comparative Omics-Driven Genome Annotation Refinement: Application across Yersiniae," PLoS ONE, Mar. 2012, vol. 7, Issue 3, 14 pages.
Examiner Requisition and Examination Search Report for Canadian Application No. 2,917,606 dated Feb. 20, 2017, 5 pages.
Extended European Search Report issued in European Patent Application No. 14856039.4 dated Oct. 27, 2017, 11 pages.
Office Action issued in Chinese Application No. 201480042342.8 dated Dec. 18, 2017, 33 pages.
Office Action issued in Australian Application No. 2017200578 dated Jan. 31, 2018, 4 pages.
Office Action issued in Chinese Application No. 201480042342.8 dated Aug. 15, 2018, 7 pages.
Office Action issued in Japanese Application No. 2016-530109 dated Aug. 7, 2018, 8 pages.
Office Action issued in Australian Application No. 2017200578 dated Aug. 24, 2018, 3 pages.
Office Action issued in Canadian Application No. 2,917,606 dated Feb. 2, 2018, 6 pages.
Office Action issued in Japanese Application No. 2016-530109 dated Nov. 20, 2018, 6 pages.
Office Action issued in Canadian Application No. 2,917,606 dated Dec. 13, 2018, 4 pages.
Office Action issued in European Patent Application No. 14 856 039.4 dated Nov. 11, 2019, 5 pages.
Office Action issued in Korean Patent Application No. 10-2016-7005127 dated Sep. 24, 2020, 14 pages.
Office Action issued in Korean Patent Application No. 10-2016-7005127 dated Mar. 26, 2021, 6 pages.

\* cited by examiner

DISCOVERY ROUTING SYSTEMS AND ENGINES

This application is a divisional of U.S. application Ser. No. 16/153,563 filed Oct. 5, 2018, which is a continuation of U.S. application Ser. No. 14/445,025 filed Jul. 28, 2014, and claims priority to U.S. Application 61/859,137, filed Jul. 26, 2013. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is computational analysis of high-volume data, especially as it relates to discovery routing systems and methods for medical data.

BACKGROUND

The background description includes information that may be useful in understanding the present invention. It is not an admission that any of the information provided herein is prior art or relevant to the presently claimed invention, or that any publication specifically or implicitly referenced is prior art.

With the advent of the numerous "-omics" sciences: genomics, proteomics, glycomics, immunomics, or brain-omics, for example, larger amounts of data are available than ever before, making analysis and even detection of relevant information overwhelming. For example, the amount of genomic data when sequenced to a statistically significant degree can easily exceed several terabytes of information, rendering any meaningful non-automated analysis impossible. To overcome this problem, automated systems can be used to identify anomalies by comparing data with reference thresholds. While such automated systems will identify outliers such as false positives and false negatives, the identification of outliers are, in most cases, still too frequent for one expert to review. For example within genomic, one mutation may be an indicator of a disease-causing genotype or it may be a silent mutation, which is relatively common.

To reduce the quantity of relevant information, an at least partially automated system can focus on single diseases or disorders to arrive at a dataset manageable for clinicians. For example, moles on the skin can be benign or malignant and can be imaged by a patient as described in U.S. patent application publication 2012/0008838. Here, a user registers and provide images of their skin to a system that then automatically analyses the images for characteristics of melanoma. A confidence value is generated, and if the value exceeds 50%, then the user can receive a recommendation to consult a physician or a referral to one or more specialists in the user's geographic location. While such a system provides a relatively robust analysis and expert follow-up, various drawbacks still remain. Most significantly, the diagnostic scope of such systems is limited to specific diseases, and within such disease to cases where the most determinative characteristics are already known.

In another example of partially automated analysis (see e.g., U.S. patent application publication 2004/0122790) a dataset is analyzed via a computer-assisted data operating algorithm to generate a result dataset identifying a feature of interest. Changes in the result dataset are then monitored based on input from a human expert. In one embodiment, the algorithm includes accessing image data derived from a medical imaging system, and supplemental data from an integrated knowledge base including clinical and non-clinical data from a plurality of controllable and prescribable resources. Although this method improves data analysis by integrating data from multiple sources, human input, a limiting resource is still required to refine the analytical algorithms. Still further, and as already noted above, such systems are typically limited to a limited set of conditions and findings.

Automated analysis is also known for non-imaging uses, as for example, discussed in U.S. patent application publication 2008/0091471. The '471 system assesses the immunological status of individuals in a patient population by establishing a database comprising a plurality of records of information each representative of the immune status of an individual in the population, processing the information in the database to find trends or patterns relating to the immune status of individuals in said patient population, and using the trends or patterns as part of a health care related decision-making process. Correlations are then generated between variables or fields in the database, and for each correlation a hypothesis is generated that may explain that correlation. Additional steps can include: automatic refuting, supporting or stating that there is insufficient data to analyze each hypothesis by further processing of the database, and reporting the correlations, their associated hypotheses and the determination to a user. While the '471 analysis advantageously improves discovery of patterns in relatively large datasets various difficulties still remain. One example difficulty includes, the analysis is generally limited to immunologic analysis. Another difficulty is that the correlations and hypotheses are reported to a user, which lacks a component of matching each report to a specific user who is qualified to take action in a timely manner.

Likewise, a method of assessing an individual's genotype correlations was disclosed in U.S. patent application publication 2010/0293130 that generates a genomic profile for an individual from a sample, determines the individual's genotype correlations with phenotypes by comparing the individual's genomic profile to a current database of human genotype correlations with phenotypes, and reports the results. Although this method provides an individual or a health care manager to information such as the individual's susceptibility to various diseases, this method lacks a discovery component, where the individual's genetic information becomes part of a basis for discovery of new traits. Moreover, single known genotypes may be silent or have a distinct phenotype, depending on other factors present in the patient. Such otherwise silent changes are not detected by the '130 system.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for systems and methods that automatically validate previously detected anomalies as significant and to connect experts with the validated findings for further action or analysis. Moreover, there is also a need for systems and methods that maximize the utility of experts, a limited resource, by filtering out false positives, false negatives, and outliers.

SUMMARY OF THE INVENTION

The inventive subject matter provides apparatus, systems, and methods that improve on the pace of discovering new practical information based on large amounts of datasets collected. In most cases, anomalies from the datasets are automatically identified, flagged, and validated by a cross-validation engine. Only validated anomalies are then associated with a subject matter expert who is qualified to take action on the anomaly. In other words, the inventive subject matter bridges the gap between the overwhelming amount of scientific data which can now be harvested and the comparatively limited amount analytical resources available to extract practical information from the data. Practical information can be in the form of trends, patterns, maps, hypotheses, or predictions, for example, and such practical information has implications in medicine, in environmental sciences, entertainment, travel, shopping, social interactions, or other areas.

In further preferred aspects, vast quantities of data can be collected in fields of inquiry including: genomics, proteomics, glycomics, brainomics, immunomics, high throughput screening, microarray technology, and lab-on-a-chip experiments. Other sources of data include data aggregated by commercial, financial, social, or self-reported sources. In addition to the enormous amounts of data, it is also necessary in many cases to perform multivariate analysis in order to elucidate phenomena. Automated data analysis systems are suited to solve problems requiring multivariate analysis, because of the inherent ability of such systems to rapidly manipulate enormous volumes of data.

In one contemplated embodiment of the inventive subject matter, a knowledge database stores datasets comprising descriptor-value pairs. Coupled to the knowledge database is an analytical engine, which assigns a qualifier to each descriptor-value pair. It is further generally preferred that an anomaly is identified if a value lies outside the bounds of a threshold given for the descriptor. When an anomaly is identified, the associated dataset is flagged. Because anomalies can arise for reasons such as experimental error or instrumental detection limits, some anomalies are better classified as analytically insignificant deviations, changes that are irrelevant to a normal or otherwise desired state (e.g., silent mutations), artifacts, outliers, false positives, or false negatives, for example. The number of such anomalies can be too great for the available subject matter experts to review, and the inventive subject matter seeks to separate analytically insignificant deviations from those anomalies that can lead to discovery and/or proper and rapid diagnosis.

To arrive at a dataset that can be managed by a subject matter expert, a cross-validation engine screens the flags, and upon validation, confirms the flag. Most preferably, the cross-validation engine uses one or more resources that are related to the anomaly, typically using a secondary parameter that is not directly linked to the anomaly (e.g., contextual data or patient history or second independent patient test). A next step is to match the confirmed and flagged anomaly with a subject matter expert capable of resolving the anomaly or otherwise taking appropriate action.

One should appreciate that the disclosed techniques provide many advantageous technical effects including rapid pre-analysis for large datasets that can then be further analyzed for clinical or other significance prior to association with a subject matter expert (or expert system). Moreover, contemplated systems and methods will also allow in-transit analysis to further enhance processing capabilities.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
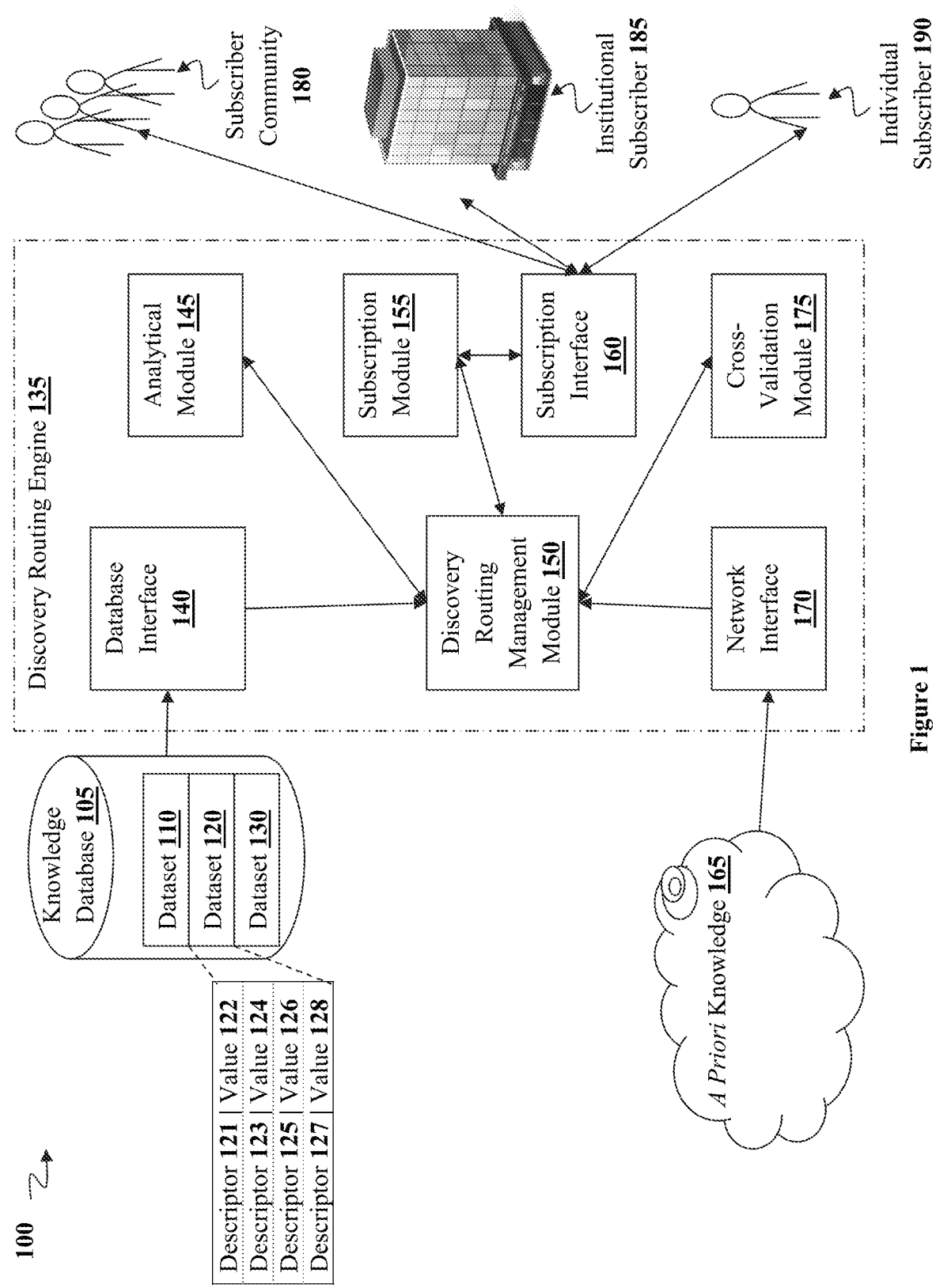
FIG. 1 depicts an example discovery routing system of some embodiments.

It should be noted that any language directed to a computer should be read to include any suitable combination of computing devices, including servers, interfaces, systems, databases, agents, peers, engines, modules, controllers, or other types of computing devices operating individually or collectively. One should appreciate the computing devices comprise a processor programmed to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the inventive subject matter are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the inventive subject matter are approximations, the numerical values set forth in the specific examples are reported as precisely as practicable. The numerical values presented in some embodiments of the inventive subject matter may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints and open-ended ranges should be interpreted to include only commercially practical values. The recitation of ranges of values herein is merely intended to serve as a shorthand method of referring individually to each separate value falling within the range. Unless otherwise indicated herein, each individual value within a range is incorporated into the specification as if it were individually recited herein. Similarly, all lists of values should be considered as inclusive of intermediate values unless the context indicates the contrary.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the inventive subject matter and does not pose a limitation on the scope of the inventive subject matter otherwise claimed. No language in the specification should be construed as indicating any non-claimed element essential to the practice of the inventive subject matter.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The inventive subject matter provides apparatus, systems, and methods that improve on the pace of discovering new practical information based on large amounts of datasets collected. In most cases, anomalies from the datasets are automatically identified and validated by a cross-validation engine. Only validated anomalies are then associated with a subject matter expert who is qualified to take action on the anomaly. In other words, the inventive subject matter bridges the gap between the overwhelming amount of scientific data which can now be harvested and the comparatively limited amount of analytical resources available to extract practical information from the data. Practical information can be in the form of trends, patterns, maps, hypotheses, or predictions, for example, and such practical information has implications in medicine, in environmental sciences, entertainment, travel, shopping, social interactions, financial analyses, or other areas.

In further preferred aspects, vast quantities of data can be collected in fields of inquiry including: genomics, proteomics, glycomics, brainomics, immunomics, high throughput screening, microarray technology, and lab-on-a-chip experiments. Other sources of data include data aggregated by commercial, financial, social, or self-reported sources. In addition to the enormous amounts of data, it is also necessary in many cases to perform multivariate analysis in order to elucidate phenomena. Automated data analysis systems are suited to solve problems requiring multivariate analysis, because of the inherent ability of such systems to rapidly manipulate enormous volumes of data.

FIG. 1 depicts one exemplary discovery routing system 100 of some embodiments. The discovery routing system 100 includes a discovery routing management module 150, an analytical module 145, a cross-validation module 175, a subscription module 155, a subscription interface 160, a database interface 140, and a network interface 170. In some embodiments, discovery routing management module 150, the analytical module 145, the cross-validation module 175, the subscription module 155, the subscription interface 160, the database interface 140, and the network interface 170 can be implemented as software that is executable by one or more processing unit (e.g., a processor, etc.). The discovery routing system 100 is shown to be coupled with a knowledge database 105 via the database interface 140.

In the depicted example, the knowledge database 105 stores datasets 110, 120, and 130. Each dataset represents data of an entity (e.g., medical data of a patient, geological data of a geographical area, financial data of an organization, etc.). The data within the dataset can be represented by descriptor-value pairs. Each descriptor-value pair includes a descriptor associated with a value. In the depiction, dataset 120 is comprised of descriptor 121 paired with value 122, descriptor 123 paired with value 124, descriptor 125 paired with value 126, and descriptor 127 paired with value 128. For simplicity, the units of associated descriptors and values are called descriptor-value pairs.

Envisioned datasets can be generated by diverse experimental or laboratory procedures and processes, and are typically high-throughput analytic systems or "-omics" platforms. However, datasets can also be assembled from multiple individual smaller groups of (or even individual) datasets. For example, health-related datasets can include genomic data, proteomic data, glycomic data, immunomic data, or brainomic data, typically representing information relevant to a cell, a tissue, an organ, or even the entire organism. Therefore, genomic data descriptors could include chromosome number, location in a genomic sequence, the identity of a gene, a frequency of a characteristic in a population, a sequence, type of sequence (e.g., siRNA, mRNA, DNA, etc.), or an individual, a geographic location of a patient subject to the genomic analysis, or another genome-relevant classification. Associated with the descriptor is a value, such as a nucleotide identity, a base-pair identity, a sequence (raw data or processed), a polymorphism result, a sequence object (e.g., in BAMBAM format), a protein sequence, or a transcript, linked to the descriptor. In these embodiments, each dataset represents medical (or "-omic" data) for a single patient.

In addition to "-omic" data, environment-related datasets can be included in the discovery process. For example, large datasets are often generated in atmospheric or oceanic research, in engineering simulations, etc. Therefore, contemplated systems and methods allow for rapid discoveries in engineering and sciences that rely on analysis of vast quantities of environmental and other data. For example, tracking geological parameters, temperature, humidity, wind-flows, and the concentration and distribution of chemicals and particles in the atmosphere can give rise to substantial quantities of datasets. Analysis of environmental datasets can yield massive and useful information, for example, information about resource distribution. In these embodiments, each dataset represents environmental data related to a defined geographic area.

Another type of information that may be tracked and recorded is behavior-related data. The resulting behavior-related datasets can also be integrated into health-related data analysis. Alternatively, it may be desirable to track behavior related to consumer, political, commute, migration, gaming, or other activities. Yet another possible category of information includes performance-related datasets. Such datasets may be of interest to individuals, researchers, or employers. Groupings of alternative elements or embodiments of the invention disclosed herein are not to be construed as limitations. Each group member can be referred to and claimed individually or in any combination with other members of the group or other elements found herein. Similar to the health-related data, each dataset in these embodiments represents behavior data of a single person.

Given the ability to track the performance of individual in athletics, in academic environments, on the job, and in government, it is possible to implement changes in individual activity, in pedagogy, in the workplace, and in the government to affect desired outcomes and maximize resource utilization. Finally, financial-related datasets can be important to individuals who wish to manage their own resources and plan for the future. For institutions, analysis of financial-related datasets could expose criminal activity or direct resources towards the development of more accessible products. Economists can also test their hypotheses by accessing and analyzing ever greater and more nuanced financial-related datasets. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should also be appreciated that the large amounts of datasets need not necessarily be contained in a single knowledge database (e.g., proprietary database or open-access database), but that the datasets may be distributed over a network of databases that are informationally coupled to each other, or that the datasets are being analyzed in transit or even at the point of collection or generation. Thus, the datasets may be permanently or temporarily stored in a computer readable medium or memory. Depending on the particular need and other parameters, the datasets may remain unaltered, or may be modified upon storage and/or transit. Therefore, the knowledge database may be programmed to store/process or transmit between 1 and 100 datasets, between 100 and 10,000 datasets, between 10,000 and 1,000,000 datasets, and even more. Thus, the size of the database will vary considerably and may be at least 100 kB, at least 10 MB, at least 1 GB, at least 100 GB, at least 10 TB, or even larger.

In further contemplated aspects, it should be recognized that the datasets could be either obtained on a fee basis from research and other data-generating facilities, or that the datasets could be voluntarily (or even compulsorily) made available. Thus, dataset exchanges are also contemplated that broker information or make datasets available from otherwise not readily accessible sources.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor programmed to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

In the depiction in FIG. 1, discovery routing engine 135 is configured such that database interface 140 is informationally coupled to knowledge database 105. Database interface 140 is also informationally coupled with discovery routing management module 150. In the depicted embodiment, database interface 140 receives datasets 110, 120, and 130 from knowledge database 105, and conveys datasets 110, 120, and 130 to discovery routing management module 150.

Discovery routing management module 150 of FIG. 1 is informationally coupled to database interface 140, analytical module 145, subscription module 155, cross-validation module 175, and network interface 170. In the embodiment of FIG. 1, discovery routing management module 150 is programmed to receive data from database interface 140, analytical module 145, subscription module 155, network interface 170, and cross-validation module 175. Discovery routing management module 150 is further programmed to transmit or direct data to analytical module 145, subscription engine 155, and cross-validation module 175.

In the embodiment depicted in FIG. 1, network interface 170 is informationally coupled to discovery routing management module 150 and to a priori knowledge 165, which in this embodiment exists outside of discovery routing engine 135. Network interface 170 is programmed to receive data from a priori knowledge 165 and transmit or direct the data further to discovery routing management module 150.

In FIG. 1, analytical module 145 is informationally coupled to discovery routing management module 150, and is further programmed to receive data from and transmit data to discovery routing management module 150. Analytical module 145 is further programmed to operate on the data received from discovery routing management module 150.

To manage the vast quantities of data, analytical module 145 is preferably coupled with discovery routing management module 150, which provides access to data from a priori knowledge 165, subscription module 155, cross-validation module 175, and knowledge database 105. Analytical module 145 receives datasets from knowledge database 105 via discovery routing management module 150, and operates on the datasets to identify at least one anomalous descriptor-value pair.

After identifying anomalous descriptor-value pairs, analytical module 145 supplies the anomalous descriptor-value pairs to cross-validation module 175 via discovery routing management module 150. Cross-validation module 175 then acts to associate the anomalous dataset with any number of conditions or characteristics, and subsequently confirm the significance of the anomalous dataset in relation to the conditions or characteristics. Once significance of the anomalous descriptor-value pair has been confirmed, cross-validation module 175 forwards the confirmed anomalous dataset to subscription module 155, via discovery routing management module 150, to be matched with a subscriber for further action.

As discussed below in greater detail, it can be desirable to couple analytical module 145 to subscription module 155 so that expert subscribers can access and refine the algorithms, modify the thresholds used to identify anomalies, or for like reasons. As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In one embodiment, analytical module 145 assigns a qualifier to each of the descriptors, depicted in FIG. 1 as descriptor 121, descriptor 123, descriptor 126, and descriptor 127. The qualifier represents the normal state for the value as it relates to its paired descriptor, as for example the normal state of value 122 as it relates to descriptor 121. Representative 'normal' states can be selected from a priori knowledge, including published standards, automated standards, expert inputs, and can also be updated to reflect evolving understandings of the range of 'normal' values. In some embodiments, the qualifiers may be generated and assigned, at least in part, by analytical module 145. The assignment of qualifiers to a descriptor-value pair can occur at the point when the dataset to which the descriptor-value pair belongs is received/generated, or when the dataset is being processed by the analytical module 145 for identifying anomalies. The qualifier can be stored in the knowledge database 105 or in a data storage separate from the knowledge database. The qualifier can comprise a single normal value or state, multiple normal values or states, or a range of normal values or states.

Analytical module 145 is programmed to traverse the descriptor-value pairs of the datasets stored in the knowledge database 105, analyze the descriptor value pairs by comparing the values in the descriptor value pairs against their corresponding qualifiers, and determine that a descriptor value pair is anomalous based on the analysis. Analytical module 145 of some of these embodiments determines whether a descriptor-value pair is normal or anomalous based on the extent to which the value of the descriptor-value pair deviates from the qualifier. Different embodiments of the analytical module 145 use different approaches to determine anomalies in the dataset. In some embodiments, analytical module 145 applies a strict requirement in that a descriptor-value pair is anomalous when the value/state of the descriptor-value pair is not the normal value/state, is not one of the normal values/states, or is outside of the range of normal values/states. In other embodiments, analytical module 145 applies a flexible requirement in that a descriptor-value pair is anomalous when the value/state of the descriptor-value pair deviates from the normal value/state, the normal values/states, the end-points of the range of normal values/states by a predetermined threshold. The latter approach has the benefit of enabling an administrator of the discovery routing system 100, or one or more of the expert subscribers to fine-tune the abnormality determination by adjusting this threshold associated with the qualifier.

The threshold value for each descriptor are set by external standards, for example: a priori standards, statistically determined standards, standards derived by an algorithm, comparisons with historical values, comparisons with boundary conditions, predicted values, databases of standards, standards published in research articles, user-defined standards, or standards from such external sources. Alternatively or in combination or concert, internal standards can be employed in anomaly identification and can include: datasets 110, 120, and/or 130 in knowledge database 105, standards calculated by extrapolation or other mathematical manipulations of such datasets, datasets that model known normal or abnormal conditions, etc. In other embodiments, the threshold value for the descriptor can result from analysis of confidence factors, multivariate analysis, or machine-learning. An anomaly is defined as a deviation of the value within a descriptor-value pair from the corresponding qualifier. Upon anomaly identification, analytical module 145 marks or directs the anomalous dataset to be operated on by cross-validation module 175.

Anomaly identification can be illustrated using examples involving nucleic acids (DNA, cDNA, RNAs, mRNA, tRNA, siRNA, μRNA, ncRNA, fRNA, rRNA, ribozymes, etc.). For nucleic acid samples, measures of 'normal' can include: identity of nucleotides or sequences, homology of nucleotides or sequences, percent identities, product peptides, the activity of enzymatic or other cellular processes, or numerical values (e.g., sequence length, copy number, protein sedimentation coefficient, ribozyme activity). With respect to peptides, measures of 'normal' can include: sequence, structural and folding structures, charge distribution, structural and folding predictions, or peptide derivatives. Such measures are preferably normalized against, copy number, strand breaks, abstractions, and circular extra-chromosomal nucleic acids. It is also preferred that analytical module 145 is programmed to incorporate feedback into the analysis performed in order to refine anomaly identification, for example by implementing a machine learning protocol. Such an analytical module can evaluate datasets using a first pass normal, and using known correlations between other relevant datasets, generate an adaptive normal, which can then be used to reevaluate the datasets and in evaluation of subsequent datasets. Therefore, it should be recognized that analytical engine 145 can be programmed to identify anomalies that are relatively simple to find (and where anomalies are based on previously known parameters and/or statistically determined parameters).

FIG. 1 also depicts cross-validation module 175, which is informationally coupled to discovery routing management module 150, and is further programmed to receive data from and transmit data to discovery routing management module 150. Cross-validation module 175 is further programmed to operate on the data received from discovery routing management module 150. In one embodiment, discovery routing management module 150 is programmed to convey a priori knowledge 165 to cross-validation module 175. A priori knowledge 165 comprises historical data, articles, publications, journals, reference texts, experiment results, lab reports, data analysis, analytical reports, and other sources of data that inform the cross-validation of anomalies significant to a condition or characteristic of interest. In some embodiments, cross-validation module 175 can retrieve a priori knowledge 165 from websites, online articles, third party databases, library databases, etc. via network interface 170.

In contrast to the potential ease and simplicity of anomaly detection by analytical module 145, cross-validation module 175 refines anomaly identification, generating sets of anomalies that have the potential to lead to new discoveries when placed in the hands of subject matter experts. The anomaly that is verified to have the potential to lead to new discoveries are designated as a significant anomaly. Viewed from another perspective, cross-validation module 175 acts to identify further attributes related to any number of conditions or characteristics of interest that have not been previously known or determined. Most preferably such attributes will use different parameters than those used by analytical module 145.

In some embodiments, cross-validation module 175 of some embodiments is programmed to first identify a possible condition associated with the anomaly. The possible condition can be identified by traversing a priori knowledge 165 from the knowledge database 105 or from the outside source via network interface 170 that includes websites, articles, publications, medical journals, etc. The a priori knowledge can provide suggestion or clue that the anomaly is associated with one or more possible condition (e.g., a disease, etc.). When the possible associated condition is identified, cross-validation module 175 cross-references additional data in the knowledge database 105 (e.g., traversing the same dataset that the anomaly was found (e.g., dataset 120)) to determine if there exists additional data that can verify the associated condition.

For example, and with respect to cross-validation module 175 depicted in FIG. 1 and similar constructs, if variation of a single nucleotide of a patient is determined to be a mutation, whether the mutation is a harmless silent mutation or is instead involved in disease development can be verified by cross-analysis of symptoms, results of a blood test, urine test, biopsy, sonogram, x-ray, MM, or other laboratory test associated with the same patient.

If, for example, a mutation is found in conjunction with upregulation of VEGF, tumorigenesis is likely underway, and the mutation is less likely to be silent. Other factors that could be used to cross-validate a mutation include examination of a patient's phenotype and/or genotype, paternal/maternal phenotype and/or genotype, family history, phylogenetic tree, or community characteristics. Information about patients can be accessed from electronic medical records among other resources, which can be stored in knowledge database 105, other databases, or accessed remotely.

In further contemplated embodiments, de novo analysis of datasets can reveal correlations that give rise to an internally generated predictive normal, which can further improve the anomaly identification refinement function of cross-validity module 175. For example, in the analysis of genomic data, computer programs and databases such as Pathway Recognition Algorithm Using Data Integration on Genomic Models (PARADIGM) database, which is further described in International Publication WO2011/139345 to Charles J. Vaske et al., filed on Apr. 29, 2011 and International Publication WO 2013/062505 to Charles J. Vaske et al., filed on Oct. 26, 2011, which are incorporated herein by reference in their entireties. PARADIGM can be used to elucidate mechanistic relationships between pathways coded in genomic datasets. The predictive normal can then be validated by external standards or internal controls, such as: a priori knowledge, journals, standard medical practices, other databases, and other subject matter-related references.

Even when an anomaly is verified, routing a particular anomalous dataset to a subscriber is not necessary when the anomaly is well characterized (and thus, not designated as a significant anomaly). For example, if an anomaly is verified by internal controls, external controls, or other known standards for the anomaly, the anomalous dataset will not be validated as a significant anomaly, and because an opportunity for discovery is absent the dataset will not be associated with a subscriber. However, if cross-validation reveals, for example, a disease condition is associated with the anomaly, and the underlying connection between the disease condition and the anomaly is unknown, then cross-validation module 175 confirms the significance of the anomaly, and the anomalous dataset is routed to any number of subscribers for discovery.

One way datasets, dataset 120 for example, can be annotated to denote significance is using a $D(n_1, m_1, x_1)$ format. Analytical module 145 can use any of the three parameters to indicate significance against a matrix of n's, m's, and x's. When an anomalous descriptor-value pair, as example descriptor 121 and value 122, from dataset 120 is identified, the descriptor-value pair is characterized as of interest, $D'(n_1, m_1, x_1)$. The of interest descriptor-value pair, $D'(n_1, m_1, x_1)$, is then run against the matrix of all other n's, m's, and x's, i.e., $n_{2-N}$, $m_{2-N}$, $x_{2-N}$. The datasets used for verification can themselves be normal, of interest, or not of interest. The of interest status of $D'(n_1, m_1, x_1)$ will be validated if an anomaly is found for at least one additional parameter in the parent dataset, dataset 120. To illustrate anomaly verification, when $n_1$ is found to be anomalous within $D(n_1, m_1, x_1)$, the dataset of interest, $D'(n_1, m_1, x_1)$, will be confirmed if $m_1$ and/or $x_1$ is also found to be anomalous. Further, if the correlation between the anomalous $n_1$ and $m_1/x_1$ is not known, then the dataset of interest will be validated as significant and forwarded to a subject matter expert who can take appropriate action towards discovering the correlation.

Another purpose of cross-validation module 175 is to confirm the validity of a flag with respect to the deviation. Cross-validation module 175 can be programmed to cross-validate anomalous descriptor-value pairs by performing a comparison with a second dataset, an a priori standard, a statistically determined standard, a standard derived by an algorithm, an historical value, a boundary condition, a predicted value, or a user-defined standard. Another possible alternative may be to perform an analysis of confidence factor, multivariate analysis, or machine-learning. It can be advantageous to validate the anomalous descriptor-value pair using a protocol distinct from the protocol employed in the step of first identifying the anomaly.

In addition to validating the significance of a descriptor-value pair, the functions of cross-validation module 175 can be further expanded to include receiving a solution from a subscriber and analyzing the subscriber's solution.

In the embodiment depicted in FIG. 1, subscription module 155 is informationally coupled to discovery routing management module 150, and is further programmed to receive data from and transmit data to discovery routing management module 150. Subscription module 155 is further programmed to operate on the data received from discovery routing management module 150. Subscription module 155 is also informationally coupled to subscription interface module 160, and is programmed to transmit or direct data to subscription interface module 160. In a preferred embodiment, subscription module 155 transmits data to subscription interface module 160 after subscription module 155 has operated on the data.

In FIG. 1, subscription interface module 160 is informationally coupled to both subscription module 155 and a variety of expert subscribers. Expert subscribers are users who have expertise in a specific areas related to the datasets stored in the knowledge database 105. Expert subscribers can be a person, a community, or an organization. As depicted here, example expert subscribers include subscriber community 180, institutional subscriber 185, and individual subscriber 190. Subscription interface module 160 is programmed to receive data from and send data to subscription module 155, subscriber community 180, institutional subscriber 185, and individual subscriber 190.

In one embodiment of the inventive subject matter, subscription module 155 and subscription interface module 160 are used to subscribe expert subscribers and correspond each expert subscriber with an identifier that indicates one or more expertise. In the embodiment depicted in FIG. 1, the expert subscribers include subscriber community 180, institutional subscriber 185, and individual subscriber 190. However, the inventive subject matter contemplates a wide variety of experts as subscribers. The expert subscribers can be human experts or machine-based experts. For example, an individual person, a group of people, a business entity, a government body, a publisher, or a trade association can all act as subject matter experts who have expertise in a specific field of endeavor and subscribe to receive problems from the discovery routing system associated with the field of endeavor. It should also be recognized that the expert subscribers may be co-located in a single location or be geographically separated (e.g., different ZIP code, city, or country). Each human expert, group of people, and/or machine can provide insight that contributes to discovery and finding solutions to problems or anomalies received from discovery routing engine 135. The user interfaces for interaction between subscription interface module 160 and subscribers are preferably configured for access by: mobile devices, tablets, phablets, smart phones, audio devices, text devices, video devices, search engines, web crawlers, browsers, clouds, personal computers, or any terminal accessible to the subscriber.

In one embodiment, subscription module 155 is programmed to operate on data to match an anomaly with an subscriber by comparing the attributes contained in a subscriber's identifier with qualities or characteristics of the descriptor-value pair comprising the anomaly, the descriptor itself, any number of conditions for which the anomaly has been validated as significant, or any other information which indicates useful compatibility between a subscriber and a significant anomaly. Viewed from another perspective, the association between any number of confirmed significant anomalous descriptor-value pairs and a subscriber can depend on its corresponding identifier comprising attributes such as field of expertise, level of expertise, availability, and geographic location, among others. This association is based on the identifier assigned to each subscriber. Yet another function of subscription module 155 can be to generate an association notification. A possible extension of generating a notification is to transmit the assignment notification to a recipient such as: an identified expert subscriber, knowledge database 105, subscription module 155, subscription interface module 160, analytical module 145, cross-validation module 175, or a third party. The association notification can be formatted for transmission to: a mobile device, a tablet, a phablet, a smart phone, an audio device, a text device, a video device, a search engine, a web crawler, a browser, a cloud, a personal computer, or any interface accessible to the recipient.

Subscriptions can be predetermined (e.g., where the expert is a computer, by provision in an employment contract, as a condition to receipt of funding, etc.) or initiated/ executed following identification of an expert that is associated with an expertise related to the anomaly. Providing an opportunity to subscribe after association with a problem or anomaly advantageously enables the system to adapt when new problems or anomalies arise and the need to seek a subscription from an appropriate expert in advance was not foreseeable. In some embodiments, subscription interface module 160 has search capabilities to identify experts when post hoc subscription is desired.

In addition to allowing flexibility in the timeline for subscription initiation, the term of each subscription can vary, for example: on a per-engagement basis, for limited or specified durations in time (e.g., daily, weekly, monthly, biannual, annual, biennial, etc.), on a challenge or competition basis (e.g., subscribers compete to find a solution, and the term ends after the first acceptable solution is discovered), or into perpetuity. Subscriptions can be maintained voluntarily, on a fee basis, on an award basis, by contract, or by other forms of engagement. Experts can be identified by self-identification, assignment, searching, assimilation of existing directories, academic credentials, references, referral, inference, or prediction. Subscription can be controlled by an organizer, or open-platform (e.g., wiki-genomics, arXiv.org, and PLoSONE.org), by automated systems, or by registration services. In some example systems, subscribers having expertise in the same area can compete (e.g., by submitting applications) or bid for access.

The identifier of each subscriber can comprise any number of attributes or characteristics, including professional expertise (e.g., oncologist, cardiologist, mycologist, dietician, geologist, physicist, statistician, etc.), descriptor, availability, location, impact factor, peer or consumer rating, performance score, etc. Therefore, the format for the identifier may vary considerably and may be a coded identifier (in which one or more properties are encoded in numerical or otherwise machine readable format), a set of meta data attached to personal or professional identification (e.g., name, title, affiliation, address, etc.), or may be provided as a log-in credential. Additionally, each problem or anomaly can be matched to more than one expert, independently, as a team (either self-identified or assigned by discovery routing engine 135 or other system), as part of a larger group of associated experts, or in conjunction with a machine expert. In some fields, such as particle physics, it is customary for research teams to be composed of numerous researchers who may subscribe independently or jointly. In still further embodiments, experts can be involved with the generation (e.g., independently, directly, or indirectly) of data that are subject to analysis in the analysis engine. For example an expert subscriber could be a researcher or director of a facility that sequences and analyses genomes.

Most typically, subscription module 155 is informationally coupled with at least one of knowledge database 105, analytical module 145, and cross-validation module 175. In the embodiment depicted in FIG. 1, subscription module 155 is informationally coupled with knowledge database 105, analytical module 145, and cross-validation module 175 via discovery routing management module 150. In some embodiments, subscription interface module 160 or subscription module 155 grant subscribed experts access to the anomalous descriptor-value pairs, the data set from which the descriptor-value pairs were derived, and/or further datasets stored in knowledge database 105. Moreover, it may be desirable that the subscriber associates further datasets with his identifier to allow cross-connection with other data and even other subscribers. Similarly, the subscription interface module 160 can be embedded in subscription module 155, the two can be collocated, and/or both can be further embedded in knowledge database 105.

It can be desirable for control and maintenance of knowledge database 105 and the subscription data to be joint or separate depending on the circumstances of data entry, spatial constraints, power constraints, regulation, or other considerations. In further envisioned embodiments, subscription module 155 is coupled to analytical module 145. Such coupling is particularly advantageous where the subscriber desired to modify the analytic protocol (or even scope of dataset) to experiment in silico or set alternate constraints for analysis. Such modification by the subscriber may be performed in an automated fashion, or via operator input (in such case, subscription module 155 and/or subscription interface module 160 may be configured as a graphical user interface).

In FIG. 1, subscription module 155 is shown coupled to discovery routing management module 150, which provides data flow to analytical module 145 and cross-validation module 175. This coupling arrangement allows subscription module 155 to access the confirmed significant anomalous descriptor-value pairs and implicated conditions needed to perform the association of expert subscribers with validated anomalies. Moreover, the expert is also enabled to modify cross-validation protocols to further refine analysis and/or cross-validation. Thus, the data transfer between subscription module 155 and the modules coupled with discovery routing management module 150 can take the form of permanent information exchange (including learning), transient information exchange, information transfer, batch protocol, etc.

An exemplary case where the expert subscriber is machine-based includes programming a computer to perform specialized analytical steps such as multivariate analysis. An algorithm can also be implemented to supply expert data analysis, interpretation, graphs/plots, charts, tables, or similar functions. Algorithms can be run in parallel to enhance the rate of data analysis or to, at least partially, simultaneously investigate alternative hypotheses or solutions. The capabilities of machine-based experts can be refined by employing machine-learning technology. Insight provided by expert subscribers can also be integral to making predictions about future outcomes and developing strategies for achieving desired outcomes.

In a preferred embodiment of the discovery routing system 100 depicted in FIG. 1, knowledge database 105 contains a series of datasets, including 110, 120, and 130. Dataset 120 is comprised of descriptor-value pairs including descriptor 121 and value 122, descriptor 123 and value 124, descriptor 1225 and value 126, and descriptor 127 and value 128. Dataset 120 is transmitted from knowledge database 105 to database interface module 140, and subsequently transmitted to discovery routing management module 150. Discovery routing management module 150 routes dataset 120 to analytical module 145 to identify any number of anomalous descriptor-value pairs. Analytical module 145 then transmits to discovery routing management module 150 any descriptor-value pairs identified as anomalous, for example (i) descriptor 121 and value 122 and (ii) descriptor 125 and value 126.

Further, upon receipt of the anomalous descriptor value pairs, discovery routing management module 150 transmits the anomalous pairs to cross-validation module 175 to validate the significance of the anomalous descriptor-value pairs. As mentioned above, the cross-validation module 175 retrieves a priori knowledge 165 via network interface 170 information that provides clues or suggests that the anomalous descriptor-value pairs (the anomaly) is associated with a possible condition. Cross-validation module 175 traverses the cross-validation data to determine first if an anomalous descriptor-value pair has a suggested association with any condition or characteristic of interest. If an association exists between an anomalous descriptor-value pair and any number of conditions or characteristics of interest (e.g., a disease), then cross-validation module 175 traverses dataset 120 to determine whether other descriptor-value pairs in dataset 120 validates/confirms the association/relationship between the anomalous descriptor-value pair and the associated conditions or characteristics. If cross-validation module 175 finds secondary confirmation of a relationship between an anomalous descriptor-value pair and any number of the identified conditions or characteristics, for example descriptor 121 and value 122, then cross-validation module 175 designates that the anomalous descriptor-value pair is significant and transmits the confirmed significant anomalous descriptor-value pair to subscription module 155 via discovery routing management module 150. If no secondary confirmation is identified, then the anomalous descriptor-value pair is unconfirmed, for example descriptor 125 and value 126, and is not transmitted to subscription module 155.

In some embodiments, cross-validation module 175 does not designate all anomalous descriptor-value pair with confirmed/validated secondary data. For example, cross-validation module 175 of some embodiments does not designate the anomalous descriptor-value pair when there is a priori knowledge showing a strong relationship (e.g., causal relationship, correlation, etc.) between the anomaly associated with the anomalous descriptor-value pair and the associated condition. The reason for this exception is that the anomalous descriptor-value pair no longer leads to discovery of new information as there is ample information related to the association between the descriptor-value pair and the associated condition.

Also in this set of embodiments, subscription module 155 collects information sourced from subscribers, such as subscriber community 180, institutional subscriber 185, and individual subscriber 190, via subscription interface module 160. Subscription module 155 can import the user data to populate attributes comprising each subscriber's identifier. Alternatively or in combination, subscription module 155 can use the user data to generate all or additional attributes comprising each subscriber's identifier. Upon receipt of a confirmed significant anomalous descriptor-value pair, subscription module 155 compares the descriptor-value pair, the condition, and/or the characteristic of interest with the each subscriber's identifier to find a match. When matches are found, subscription module 155 can generate and send notifications, via subscription interface 160, to at least some of the matched subscribers, notifying them of the confirmed significant anomalous descriptor-value pair as a discovery of interest regarding the associated conditions or characteristics.

Figure 2:
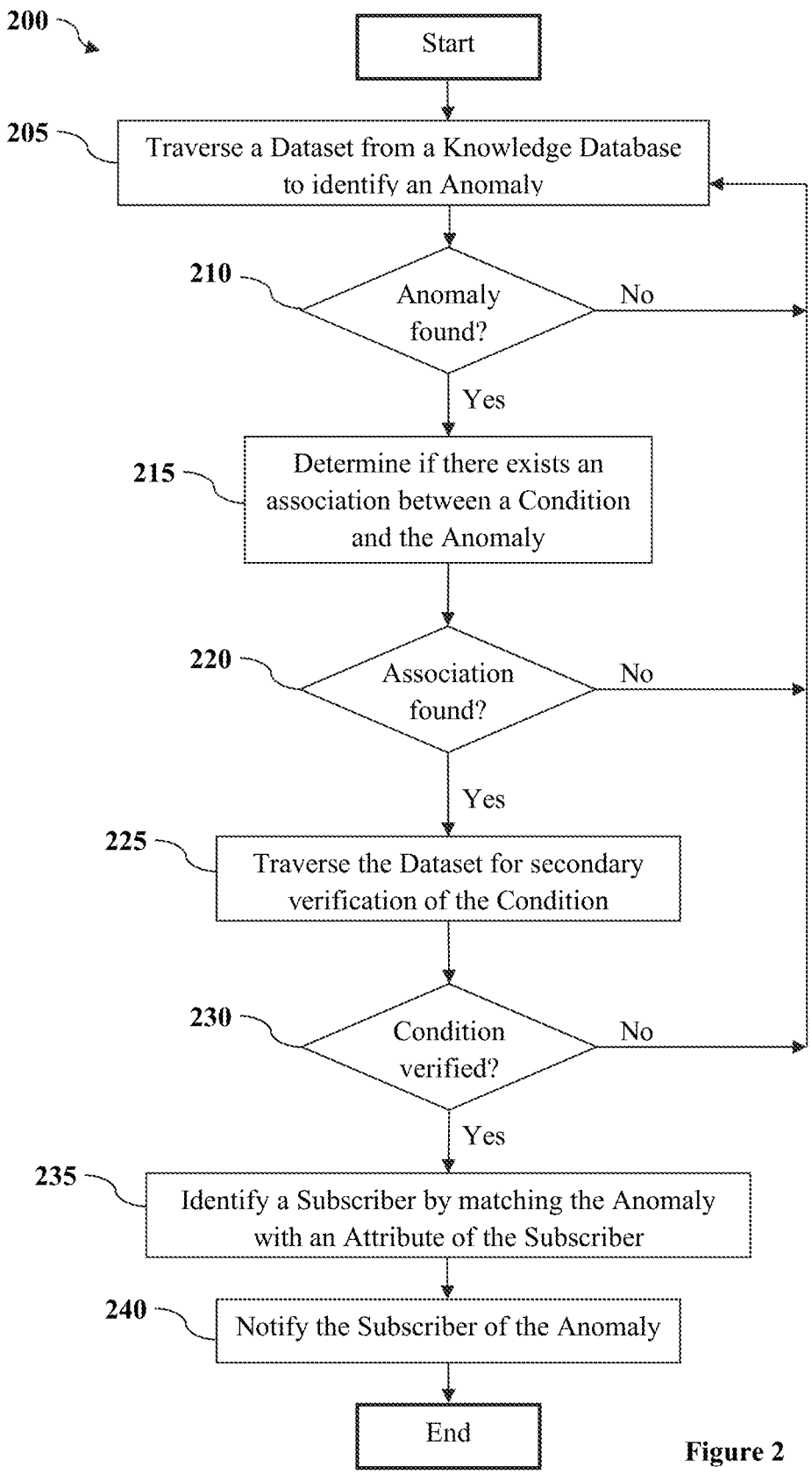
FIG. 2 illustrates a process for routing anomalies to different expert subscribers for discovery.

FIG. 2 illustrates a process 200 for routing discoveries. The process 200 begins by traversing (at step 205) a dataset from a knowledge database and evaluating the data to identify an anomaly. The dataset can be analogous to datasets 110, 120, and 130 in FIG. 1. The knowledge database can be analogous to knowledge database 105 in FIG. 1. The identification of an anomaly can occur in a manner analogous to the function of analytical module 145 in FIG. 1, including the comparison of the value from each descriptor-value pair in the datasets with a qualifier, which can comprise a normal value for the related descriptor and a threshold interval for the normal value. If it is determined that there is an anomaly in the descriptor-value pair at step 210 (i.e., the value in a descriptor-value pair differs from the normal beyond the threshold, then the process 200 proceeds to step 215 to determine if there exists an association between the anomaly and a condition. On the other hand, if there is no anomaly found in the description-value pair, the process 200 returns to step 205 to continue to traverse the dataset to find the next descriptor-value pair. Thus, each descriptor-value pair is evaluated in turn: if no anomaly is detected, then the next descriptor-value pair is evaluated.

When an anomalous descriptor-value pair is detected, the next step in the process 200 is determine (at step 215) if there exists an association between a condition and the anomaly. This determination can be executed in a manner analogous to the function of cross-validation module 175 in FIG. 1. This step can include traversing a priori knowledge, such as articles, websites, reference texts, or a priori knowledge 165 in FIG. 1, for suggestions of an association between the anomalous descriptor-value pair and any condition or characteristic of interest. If no association between a condition or characteristic of interest and the anomalous descriptor-value pair is found at step 220, then the process 200 returns to step 205 to traversing the dataset from the knowledge database to identify an anomaly from another descriptor-value pair. If an association is detected between the anomalous descriptor-value pair and a condition or characteristic of interest at step 220, the process 200 proceeds to step 225 to traverse the dataset for secondary verification.

After identifying an association between the anomalous descriptor-value pair and a condition or characteristic of interest, the next step 225 is to traverse the dataset from which the anomalous descriptor-value pair is derived and search for secondary verification of the condition or characteristic of interest. This step 225 can be performed in a manner analogous to the function of cross-validation module 175 in FIG. 1. The search for secondary verification of the condition or characteristic of interest, which was identified in the previous step of searching for an association between the anomalous descriptor-value pair and a condition or characteristic of interest, can include traversing a priori knowledge, such as articles, websites, reference texts, or a priori knowledge 165 in FIG. 1. If any descriptor-value pair in the dataset, other than the identified anomalous descriptor-value pair, is identified as related to the identified condition or characteristic of interest at step 230, then the anomalous descriptor value pair has been verified as significantly related to the condition or characteristic of interest and the process proceeds to step 235 to identify a subscriber. If no relation between a descriptor-value pair in the dataset and the condition or characteristic of interest at step 230, then the process 200 returns to the step 205 to traverse the dataset to identify other anomalous descriptor-value pairs.

Once an anomalous descriptor-value pair has been verified as significantly related to a condition or characteristic of interest, the process proceeds to the next step 235 to identify a subscriber by matching the anomaly with an attribute of the subscriber. This step can be performed in a manner analogous to subscription module 155 in FIG. 1. Subscribers are identified based on assigned identifiers, which comprise attributes of each subscriber. The identifiers of at least some of the subscribers are traversed to identify a match between the attributes of a subscriber and the anomalous descriptor-value pair, the anomalous descriptor, the anomalous value, and/or the related condition or characteristic. Once a subscriber has been matched with the anomaly, the subscriber is notified of the anomaly at step 240.

Figure 3:
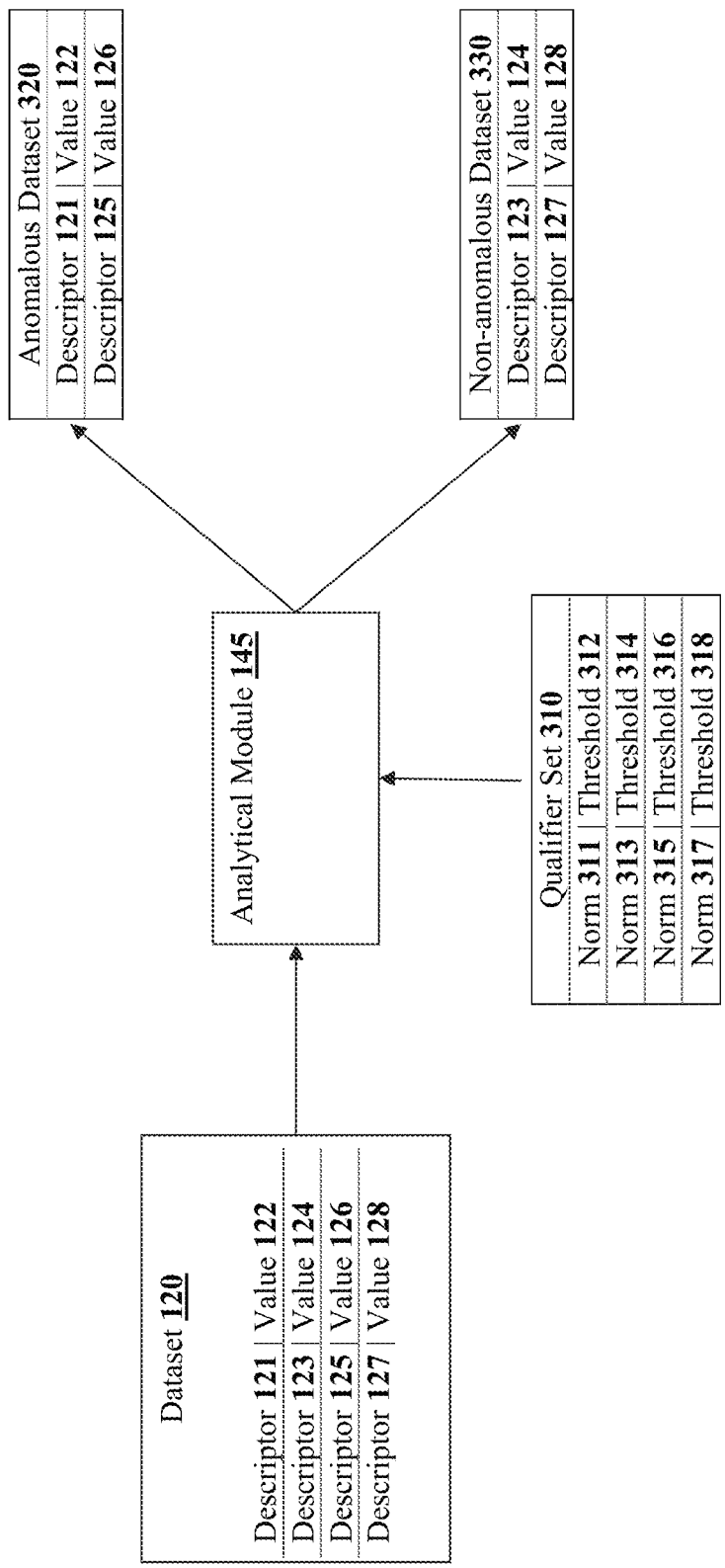
FIG. 3 depicts an analytical module in details.

FIG. 3 depicts one embodiment of analytical module 145. Dataset 120 is comprised of a number of descriptor-value pairs, descriptor 121 and value 122, descriptor 123 and value 124, descriptor 125 and value 126, and descriptor 127 and value 128. Dataset 120 can be transmitted to analytical module 145 for operation. Qualifier set 310 is comprised of norms with related thresholds, including norm 311 and threshold 312, norm 313 and threshold 314, norm 315 and threshold 316, and norm 317 and threshold 318. Each set of norms and thresholds in qualifier set 310 is related to a specific descriptor-value pair in dataset 120. For example, norm 311 and threshold 312 is associated with descriptor 121 and value 122, norm 313 and threshold 314 is associated with descriptor 123 and value 124, norm 315 and threshold 316 is associated with descriptor 125 and value 126, and norm 317 and threshold 318 is associated with descriptor 127 and value 128. Qualifier set 310 can be transmitted to analytical module 145 for operation.

The purpose of analytical module 145 is to identify, from dataset 120 or any other input dataset, descriptor-value pairs that are anomalous. In this embodiment, anomalous is characterized by the difference between a value in a descriptor-value pair and a norm for the descriptor from the descriptor-value pair. For example, analytical module 145 operates on descriptor-value pair descriptor 121 and value 122 to determine how much value 122 differs from the norm associated with descriptor 121, here norm 311. Each threshold related to a norm is a limit, which can be set by a user, subscriber, machine, algorithm, or other active source, or can be set by a lab result, a priori knowledge, or other static source, that defines what values related to the associated descriptor will be considered an anomaly. For example, threshold 312 defines a range of values around norm 311 that are considered non-anomalous for descriptor 121. All values for descriptor 121 existing beyond the range of values defined by threshold 312 are considered anomalous.

Analytical module 145, as depicted in FIG. 3, identifies and separates anomalous descriptor-value pairs in dataset 120, or any other input dataset, from non-anomalous descriptor-value pairs. For example, and as depicted in FIG. 3, dataset 120 and qualifier set 310 are input to analytical module 145. Analytical module 145 compares value 122 with norm 311 and threshold 312. Because the difference between value 122 and norm 311 is greater than threshold 312, the descriptor-value pair of descriptor 121 and value 122 is anomalous. Viewed from another perspective, because value 122 is beyond the range of values set by threshold 312 with regard to norm 311, descriptor 121 and value 122 are considered anomalous. In this embodiment, the same operation is applied to all descriptor-value pairs in dataset 120 to characterize each descriptor-value pair as either anomalous or non-anomalous. Alternatively, analytical module 145 can be programmed to, upon identifying an anomalous descriptor-value, immediately forward the anomalous descriptor-value pair to a receiving module, interface, or user, such as discovery routing management module 150 in FIG. 1.

In the embodiment depicted in FIG. 3, analytical module 145 operates on all descriptor-value pairs in dataset 120 and, based on the norms and thresholds in qualifier set 310, identifies descriptor-value pairs descriptor 121 and value 122 and descriptor 125 and value 126 as anomalous, and compiles anomalous dataset 320. In this embodiment, analytical module 145 also identified descriptor-value pairs descriptor 123 and value 124 and descriptor 127 and value 128 as non-anomalous, and compiled non-anomalous dataset 330. Alternatively, analytical module 145 can be programmed to identify and compile anomalous dataset 320 but not compile non-anomalous dataset 330.

Figure 4:
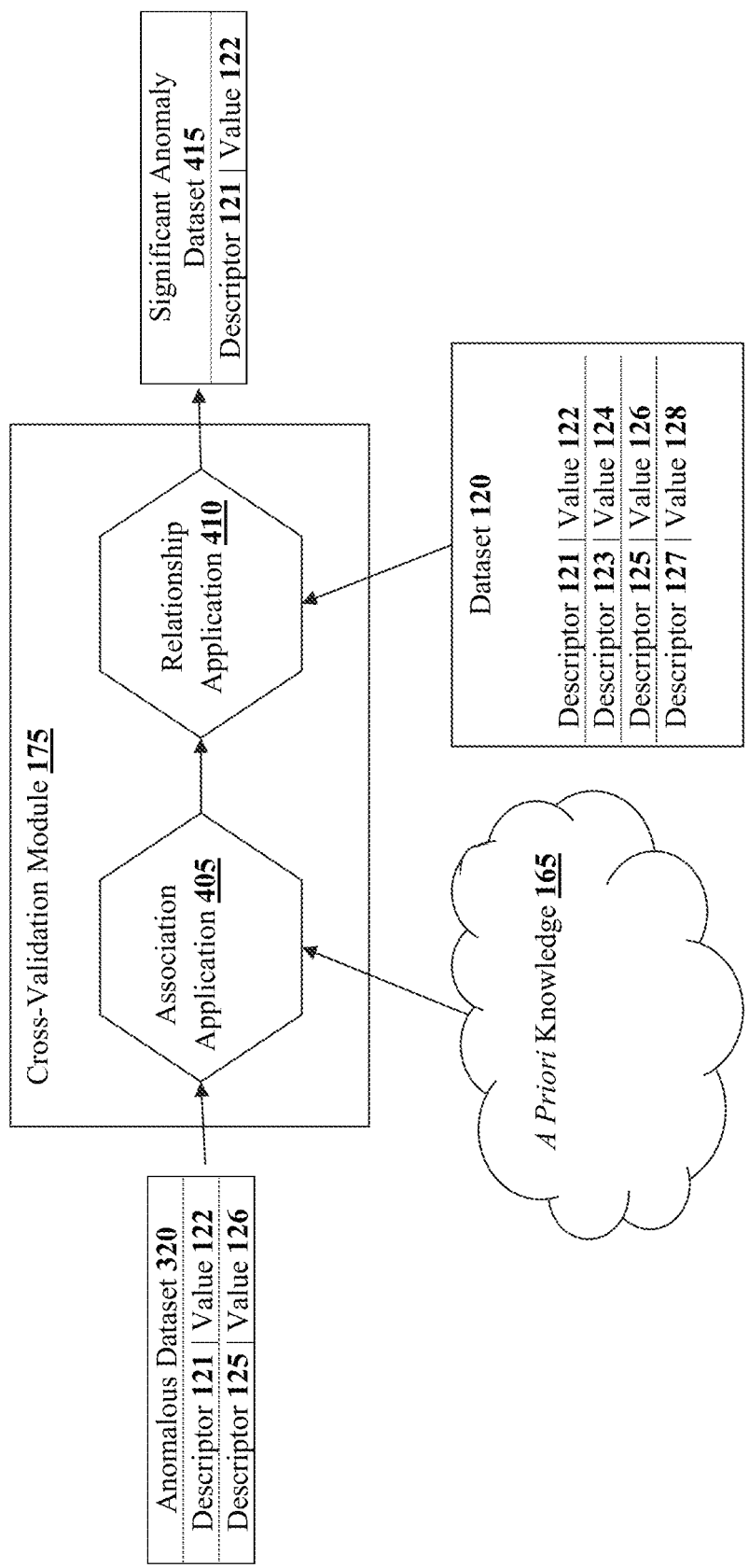
FIG. 4 depicts a cross-validation module in details.

FIG. 4 depicts one embodiment of cross-validation module 175. Dataset 120 is comprised of a number of descriptor-value pairs, descriptor 121 and value 122, descriptor 123 and value 124, descriptor 125 and value 126, and descriptor 127 and value 128. Anomalous dataset 320 is comprised of descriptor-value pairs descriptor 121 and value 122 and descriptor 125 and value 126. In one embodiment, anomalous data set 320 is transmitted to cross-validation module 175 by analytical module 145. In another embodiment, a data management module such as discovery routing management module 150 transmits anomalous dataset 320 to cross-validation module 175. A priori knowledge 165 comprises historical data, articles, publications, journals, reference texts, experiment results, lab reports, data analysis, analytical reports, and other sources of data that inform the cross-validation of anomalies significant to a condition or characteristic of interest. As depicted, cross-validation module 175 comprises association application 405 and relationship application 410. In one embodiment, cross-validation module 175 is programmed to receive anomalous dataset 320, dataset 120, and data from a priori knowledge 165, operate on the received data, and generate significant anomaly dataset 415.

The purpose of cross-validation module 175 is analogous to the description of cross-validation module 175 in FIG. 1. Cross-validation module 175 is programmed to verify an anomalous descriptor-value pair as significant in relation to a condition or characteristic of interest. In the embodiment depicted in FIG. 3, cross-validation module 175 is programmed to receive anomalous dataset 320, dataset 120, and data from a priori knowledge 165. The description-value pairs of anomalous dataset 320 are identified as anomalous description-value pairs from the dataset 120.

Association application 405 is programmed to operate on the descriptor-value pairs of anomalous dataset 320 and data from a priori knowledge 165. Association application 405 operates on the data by traversing a priori knowledge 165 for data that indicates a connection or association between a descriptor-value pair in anomalous dataset 320 and a condition or characteristic of interest. The indication of a connection or association could be, for example, an article hypothesizing descriptor 121 causes or contributes to a particular condition or characteristic. As another example, the indication could be an article identifying any number of suspected causes of a particular condition or characteristic, with descriptor 121 enumerated among the suspected causes. Association application 405 is further programmed to forward anomalous descriptor-value pairs that have been associated with a condition or characteristic of interest to relationship application 410.

As an example of the operation of one embodiment, association application 405 receives descriptor-value pairs descriptor 121 and value 122 and descriptor 125 and value 126, and receives data from a priori knowledge 165 that associates descriptor 121 and value 122 with a condition or characteristic of interest, and subsequently forwards descriptor 121 and value 122 to relationship application 410.

As depicted in FIG. 4, relationship application 410 is programmed to receive data from association application 405 and dataset 120 and to operate on the data. The purpose of relationship application 410 is to verify the significance of the anomalous descriptor-value pair that has been associated with a condition or characteristic of interest. Relationship application 410 is programmed to verify the significance by traversing data that indicates descriptor-value pairs that have a known connection with the condition or characteristic that has been associated with the anomalous descriptor-value pair by operation of association application 405. Relationship application 410 is further programmed to traverse dataset 120, or other input dataset, to identify descriptor-value pairs that have a known connection with the associated condition or characteristic, which establishes secondary verification of the significance of the anomalous descriptor-value pair. Further, relationship application 410 is programmed to compile the significant anomalous descriptor-value pairs into significant anomaly dataset 415, and forward dataset 415 to a receiving module, interface, or user, such as discovery routing management module 150 in FIG. 1. In another embodiment, relationship application 410 can be programmed to immediately forward a significant descriptor-value pair to a receiving body once significance has been established, rather than compiling all verified significant descriptor-value pairs.

As an example of the operation of one embodiment, relationship application 410 receives descriptor 121 and value 122 which have been associated with a condition or characteristic of interest. Relationship application also receives data identifying other descriptor-value pairs that have a known connection with the associated condition or characteristic, for example descriptor 127 and value 128. Relationship application 410 traverses dataset 120, identifies descriptor 127 and value 128 within dataset 120, which characterizes anomalous descriptor-value pair descriptor 121 and value 122 as significant, compiles descriptor 121 and value 122 into significant anomaly data set 415, and forwards significant anomaly dataset 415 to a receiving module, interface, or user, such as discovery routing management module 150 in FIG. 1.

Figure 5:
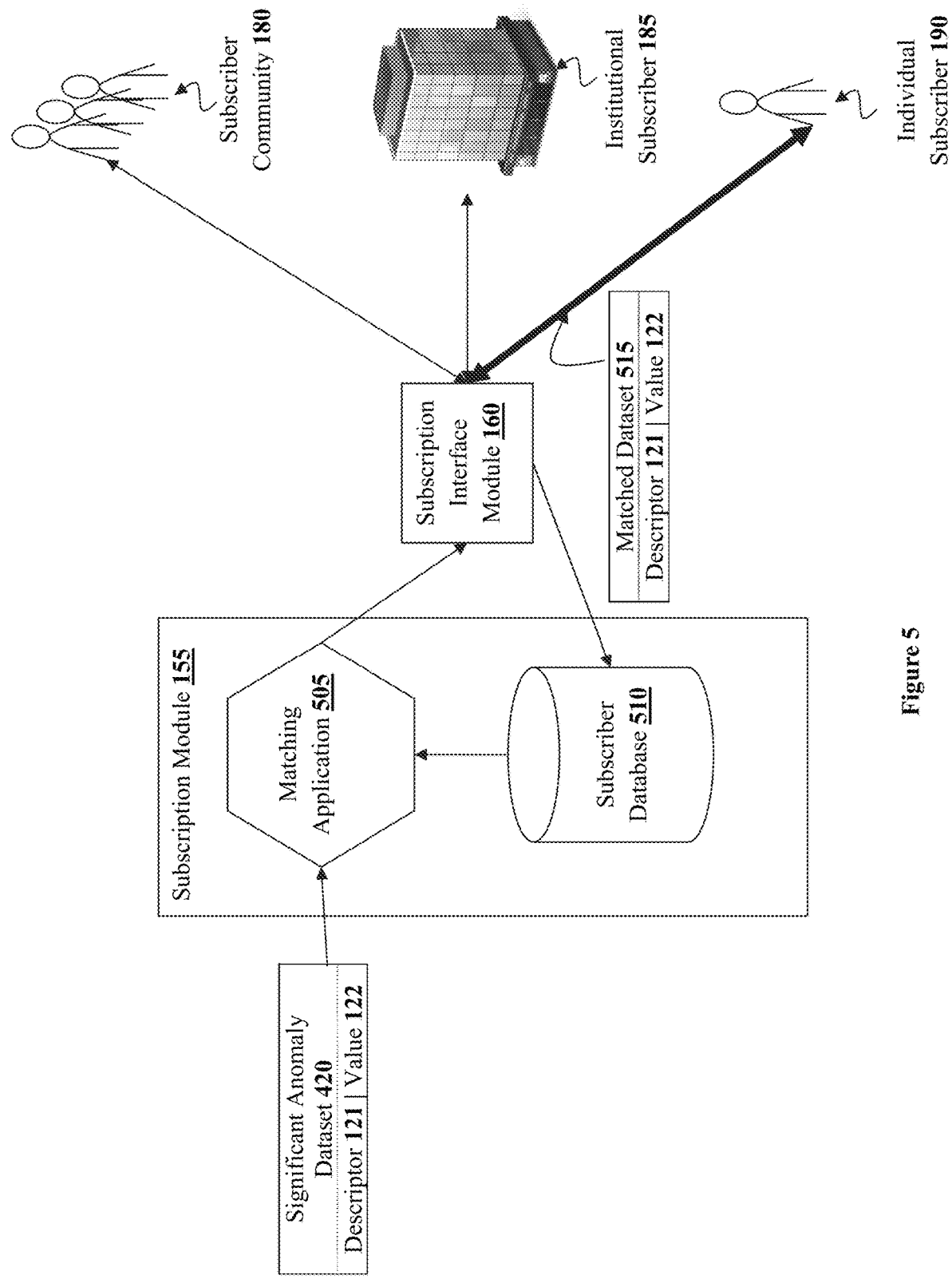
FIG. 5 depicts a subscription module in details.

FIG. 5 depicts one embodiment of subscription module 155. Significant anomaly dataset 420 is comprised of descriptor 121 and value 122, which have been verified as significant in relation to a condition or characteristic of interest by operation of, for example, cross-validation module 175. Subscription module 155 is comprised of matching application 505 and subscriber database 510. Subscription module 155 is programmed to receive data that has been verified as significant in relation to a condition or characteristic of interest from, for example, cross-validation module 175, operate on the data, and forward the operated data to subscription interface module 160. Subscription module 155 is further programmed to transmit data to and receive data from subscription interface module 160. The purpose of subscription module 155 is to match significant anomaly data set 420 with appropriate subscribers based on subscriber identifiers.

Subscriber database 510 is programmed to receive subscriber data, such as identifiers comprised of subscriber attributes or solutions to anomalies, from subscription interface module 160. Subscriber database 510 is further comprised to forward data, such as subscriber identifiers and attributes, to matching application 505 to be operated upon.

Matching application 505 is programmed to receive data, such as significant anomaly dataset 420, which has been verified as significant in relation to a condition or characteristic of interest. Matching application 505 is further programmed to receive data from subscriber database 510, including identifiers associated with each subscriber and attributes comprising the identifiers. Matching application 505 is further programmed to forward descriptor-value pairs that have been matched with a subscriber to subscription interface module 160 to be delivered to the matched describer.

Subscription interface module 160 is programmed to receive subscriber data, such as identifiers comprised of attributes of the subscriber, from subscribers, such as subscriber 180, institutional subscriber 185, and individual subscriber 190. Subscriber interface module 160 is further programmed to transmit the subscriber data to subscription module 155, and receive notification data, such as matched data set 515, from subscription module 155 and transmit the notification data to matched subscribers, such as individual subscriber 190. Subscription interface module 160 can be further programmed to receive solution data regarding any notification data, and to transmit the solution data to subscription module 155.

In one embodiment of the depiction of FIG. 5, matching application 505 receives significant anomaly data set 420 comprised of descriptor 121 and value 122, as well as receiving subscriber identifiers comprised of attributes from subscriber database 510. In this embodiment, subscriber identifiers includes attributes related to subscriber community 180, institutional subscriber 185, and individual subscriber 190 that have been entered into subscriber database 510 via subscription interface module 160. Matching database compares the descriptor-value pair descriptor 121 and value 122, descriptor 121, value 122, and the related condition or characteristic of interest with the identifiers, and comprised attributes, for each subscriber in order to identify matches. In this embodiment, descriptor-value pair descriptor 121 and value 122 is identified as a match for individual subscriber 190. Because descriptor-value pair descriptor 121 and value 122 match the identifier, and comprised attributes, with individual subscriber 190, matching application 505 forwards the data to subscription interface module 160, which in turn forwards matched data set 515, comprised of descriptor 121 and value 122, to individual subscriber 190. In some embodiments, individual subscriber 190 reports a solution for the relation between the condition or characteristic of interest and descriptor 121 and value 122 to subscription interface module 160, which adds the data to discovery routing engine 135 from FIG. 1.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be appreciated that the discovery routing system can be integrated into the Continuous Learning System illustrated in FIG. 3. Inherent in big health data is information that can give rise to new knowledge and transform conventional wisdom. Big data is fed into the discovery routing system from the Global Health Grid, accessed via the Medical Information Highway, and data aggregated data in genomics, proteomics, clinical data, imaging, demographics, and public health. By identifying anomalies that are not well understood and focusing the attention of subject matter experts on finding answers relating to those anomalies, the process of discovery is facilitated.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A computer-based method of detecting anomalies using at least one processor coupled with a memory and a knowledge database, the memory storing software instructions and the knowledge database storing a plurality of datasets, each dataset comprising at least one descriptor-value pair having a descriptor associated with a value, the method comprising:
    associating, by the at least one processor, a qualifier with at least one descriptor wherein the qualifier represents a normal state of the value as it relates to the associated descriptor and is determined using one or more representative standard values extracted from the knowledge database or at least one external database connected to the at least one processor via a network interface;
    identifying, by the at least one processor, at least one anomaly in one or more datasets of the plurality of datasets, wherein the at least one anomaly includes at least one descriptor-value pair associated with one or more conditions of interest, and a value that deviates from the qualifier associated with the at least one descriptor beyond a threshold value for the descriptor, the threshold value being determined at least in part by the processor programmed to adjust an external threshold value extracted from the at least one external database, wherein the processor incorporates feedback to automatically refine anomaly identification based on at least a portion of the plurality of datasets;
    designating, by the at least one processor, the at least one anomaly as a significant anomaly by using a cross-validation protocol distinct from the protocol used to identify the at least one anomaly, wherein the cross-validation protocol comprises receiving and analyzing information external to the one or more datasets in the knowledge database including the at least one identified anomaly, the external information derived from the at least one external database and including a user-defined standard to associate the anomaly with the one or more conditions of interest, and wherein the processor is programmed to modify the cross-validation protocol when a secondary confirmation of a relationship is found between an anomalous descriptor-value pair and the at least one identified anomaly in the one or more datasets by analyzing the plurality of datasets to determine one or more predictive standards;
    associating, by the at least one processor, the significant anomaly with the at least one human or machine-based expert; and
    communicating, by the at least one processor, with the at least one human or machine-based expert.

2. The method of claim 1, wherein the plurality of datasets is distributed over a network of databases that are informationally coupled to each other.

3. The method of claim 1, wherein the plurality of datasets is analyzed in transit or at the point of collection.

4. The method of claim 1, wherein the plurality of datasets includes data derived from a single person.

5. The method of claim 1, wherein the plurality of datasets includes environmental data related to a defined geographical area.

6. The method of claim 1, wherein the plurality of datasets includes vehicle data related to a defined geographical area and time period.

7. The method of claim 1, wherein the threshold value for the descriptor is further chosen according to at least one of the following: an a priori standard, a statistically determined standard, a standard derived by an algorithm, a comparison with historical values, a comparison with boundary conditions, a predicted value, an analysis of confidence factors, and a user-defined standard.

8. The method of claim 1, further comprising generating an association notification when the significant anomaly is associated with a human.

9. The method of claim 1, further comprising transmitting a notification to the at least one associated human.

10. An anomaly detection system comprising:
at least one processor;
a knowledge database coupled with the at least one processor, the knowledge database storing a plurality of datasets, each dataset comprising at least one descriptor-value pair having a descriptor associated with a value;
at least one memory coupled with the at least one processor, the at least one memory storing software instructions executable by the at least one processor to perform operations comprising:
associating a qualifier with at least one descriptor wherein the qualifier represents a normal state of the value as it relates to the associated descriptor and is determined using one or more representative standard values extracted from the knowledge database or at least one external database connected to the at least one processor via a network interface;
identifying at least one anomaly in one or more datasets of the plurality of datasets, wherein the at least one anomaly includes at least one descriptor-value pair having a descriptor associated with one or more conditions of interest, and a value that deviates from the qualifier associated with the at least one descriptor beyond a threshold value for the descriptor, the threshold value being determined at least in part by the processor programmed to adjust an external threshold value extracted from the at least one external database wherein the processor incorporates feedback to automatically refine anomaly identification based on at least a portion of the plurality of datasets;
designating the at least one anomaly as a significant anomaly by using a cross-validation protocol distinct from the protocol used to identify the at least one anomaly, wherein the cross-validation protocol comprises receiving and analyzing information external to the one or more datasets having the at least one anomaly, the external information derived from the at least one external database and including a user-defined standard to associate the at least one anomaly with the one or more conditions of interest, and wherein the processor is programmed to modify the cross-validation protocol when a secondary confirmation of a relationship is found between an anomalous descriptor-value pair and the at least one identified anomaly in the one or more datasets by analyzing the plurality of datasets to determine one or more predictive standards;
associating the significant anomaly with at least one human or machine-based expert; and
communicating with the at least one human or machine-based expert.

11. The system of claim 10, wherein the plurality of datasets is distributed over a network of databases that are informationally coupled to each other.

12. The system of claim 10, wherein the plurality of datasets is analyzed in transit or at the point of collection.

13. The system of claim 10, wherein the plurality of datasets includes data derived from a single person.

14. The system of claim 10, wherein the plurality of datasets includes environmental data related to a defined geographical area.

15. The system of claim 10, wherein the plurality of datasets includes vehicle data related to a defined geographical area and time period.

16. The system of claim 10, wherein the threshold value for the descriptor is further chosen according to at least one of the following: an a priori standard, a statistically determined standard, a standard derived by an algorithm, a comparison with historical values, a comparison with boundary conditions, a predicted value, an analysis of confidence factors, and a user-defined standard.

17. A non-transitory computer readable medium comprising instructions executable by a computer processor to execute processing comprising:
associating a qualifier with at least one descriptor wherein the qualifier represents a normal state of the value as it relates to the associated descriptor and is determined using one or more representative standard values extracted from the knowledge database or at least one external database connected to the at least one processor via a network interface;
identifying at least one anomaly in at least one dataset of a knowledge database storing a plurality of datasets, each dataset comprising at least one descriptor-value pair having a descriptor associated with a value, wherein the at least one anomaly includes at least one descriptor-value pair associated with one or more conditions of interest, and a value that deviates from the qualifier associated with the at least one descriptor beyond a threshold value for the descriptor, the threshold value being determined at least in part by the processor programmed to adjust an external threshold value extracted from the at least one external database wherein the processor incorporates feedback to automatically refine anomaly identification based on at least a portion of the plurality of datasets;
designating the at least one anomaly as a significant anomaly by using a cross-validation protocol distinct from the protocol used to identify the at least one anomaly, wherein the cross-validation protocol comprises receiving and analyzing information external to the at least one dataset having the at least one identified anomaly, the external information derived from the at least one external database and including a user-defined standard to associate the at least one identified anomaly with the one or more conditions of interest, and wherein the processor is programmed to modify the cross-validation protocol when a secondary confirmation of a relationship is found between an anomalous descriptor-value pair and the at least one identified anomaly in the one or more datasets by analyzing the plurality of datasets to determine one or more predictive standards;
associating the significant anomaly with at least one human or machine-based expert; and
communicating with the at least one human or machine-based expert.

18. The computer readable medium of claim 17, wherein the plurality of datasets is distributed over a network of databases that are informationally coupled to each other.

19. The computer readable medium of claim 17, wherein the plurality of datasets is analyzed in transit or at the point of collection.

20. The computer readable medium of claim 17, wherein the plurality of datasets includes data derived from a single person.

\* \* \* \* \*